United States Patent [19]

Green

[11] 4,046,013

[45] Sept. 6, 1977

[54] COMBINATION DRILL AND PLUG AND METHOD AND APPARATUS FOR USING SAME FOR EXTRACTING A FLUID SAMPLE FROM AN ELECTRICAL CABLE

[75] Inventor: Cyril Robert Green, Honesdale, Pa.

[73] Assignees: Mario D. Medio; Grace E. Medio, both of Malverne, N.Y.

[21] Appl. No.: 691,223

[22] Filed: June 1, 1976

[51] Int. Cl.² .......................... G01N 1/10; F16F 51/00
[52] U.S. Cl. .................................. 73/422 R; 137/318
[58] Field of Search ...................... 73/422 R; 29/567; 137/317, 318; 138/97

[56] References Cited

U.S. PATENT DOCUMENTS

| 537,755 | 4/1895 | Crozier | 137/318 |
| 2,661,123 | 12/1953 | Guarino | 137/318 |
| 3,302,493 | 2/1967 | Hulslander et al. | 137/318 |
| 3,349,792 | 10/1967 | Larkin | 137/318 |
| 3,821,965 | 7/1974 | Reynolds | 137/318 |

Primary Examiner—S. Clement Swisher
Attorney, Agent, or Firm—Bauer, Amer & King

[57] ABSTRACT

For extracting a test sample of fluid from a cable or the like, the present invention provides a combination drill and plug that has cutting means at one end thereof and tapered thread forming or cutting means proximate the other end thereof. When the combination drill and plug is driven forwardly by the apparatus and utilizing the method comprising the present invention, the cutting means thereof removes a mass of material in the form of chips and/or a disk and retains the mass of material so that it does not contaminate the fluid in the cable. After a suitable quantity of fluid is removed from the cable, the combination drill and plug is further advanced so that the thread forming or cutting portion thereof engages the hole formed by the drill portion and forms or cuts threads therein so as to seal the cable and permit its further usage without additional leakage of fluid.

26 Claims, 11 Drawing Figures

COMBINATION DRILL AND PLUG AND METHOD AND APPARATUS FOR USING SAME FOR EXTRACTING A FLUID SAMPLE FROM AN ELECTRICAL CABLE

BACKGROUND OF THE INVENTION

This invention relates generally to a method and apparatus for removing a fluid test sample from an electrical cable or the like and further relates to a novel, combination drill and plug that is used with the method and apparatus of this invention.

Electrical cables for the distribution of electrical power are usually manufactured in specific, predetermined lengths. Because of manufacturing limitations and economics, the greater the diameter of the cable the shorter is the length. Consequently, these cables must be connected or spliced end-to-end in order to increase the distance and coverage from the power source beyond that possible with a single length of cable. At lower voltages, splicing poses no real problem, but as the voltage increases, certain precautions must be taken to prevent failure of the splice or joint due to electrical leakage as well as to safeguard personnel from the lethal effects of the electric current. High voltages cables used underground by power companies usually comprise a multiple, usually two or three, of individually insulated conductors which are bound together and which are additionally insulated as a single group. For protection, a lead sheath and/or an insulating and abrasion resisting sheath are additionally placed over the insulated group of conductors.

For underground service, a splice or joint is made by cutting away the sheaths and the insulation for a sufficient distance to permit separation of individually insulated conductors. The insulation is then removed from each conductor for a distance of several inches or just long enough to accept a connecting sleeve which is placed over and crimped onto the bare conductors to form a secure mechanical and electrical joint. The individual splices are then heavily reinsulated using electrical tape, rubber, epoxy-fiberglass, or any other suitable material. A lead sleeve is then positioned so as to surround the splice or joint while leaving a gap between the sleeve and the spliced and insulated conductors. The end of the sleeve are rounded and formed to fit closely about the lead sheath of the cable and the sleeve and the sheath are soldered together to make a fluid-tight joint. A high quality, dry, electrically insulating oil is then pumped into the sleeve until it is filled completely at which time dry nitrogen gas at low pressure (approximately 3–7 p.s.i.) is introduced into the cable through the combination joint and its associated cables to thereby fill all of the voids. The oil improves the insulating properties of the joint or splice, keeps moisture and air away from the conductors and, in the event of a slight rupture or crack in the joint or cables, will usually seep out, thereby preventing water and air from entering in most cases. However, sometimes water will enter and then will settle in the lowest part of the system, which usually is the joint or splice. When this occurs, the joint insulation degrades and electrical leakage takes place so that the joint or splice eventually fails.

Under previously existing conditions, testing for the presence of water or moisture in the insulating oil required indentifying the suspect joint and cable system, communicating with the distribution center, turning off the current, re-identifying and testing the cable for current and then applying a certification tag to the suspect joint. Only then are the operating personnel permitted to work on the joint or splice.

In order to repair the suspected joint or splice, a hole is first drilled into the sleeve and a quantity of fluid is drained out through the hole. The fluid is collected for later testing and the hole is then plugged with a screw which is soldered to the sleeve to prevent further leakage. After this procedure has been completed, the distribution center is then notified and the power may be turned on. All of the foregoing prior art method is time consuming and costly, requiring many hours, several crews of men and costing thousands of dollars per test.

SUMMARY OF THE INVENTION

The present invention relates to a specially designed combination drill and plug as well as a machine and method for using the drill and plug in order to drill into the lead sleeve of the splice or joint in an electrical cable. The present invention provides a method and apparatus for removing and collecting a sample of fluid for testing. The combination drill and plug is then fully inserted into the drilled hole in order to seal the opening. This may be accomplished without interrupting the flow of current and, for safety, from a remote location with the operator outside the manhole in which the spliced joint is located. The entire operation of the present invention which comprises applying the apparatus to the joint or splice, the extraction of the sample, the subsequent sealing and removal of the apparatus by a single, two-man crew, takes only a few minutes from start to finish.

One aspect of the present invention resides in the combination drill and plug which includes a hexagonal or other suitably shaped head for driving, a point which enters the metal to be pierced and serves to stabilize the combination drill and plug, a cylindrical portion having two ears which serve as the drilling portion and a tapered threaded portion. The two ears cut a plug of metal around the point while the sharp end of the cylindrical portion cuts away the underside of the plug thereby reducing its thickness. An annular groove in the combination drill and plug of the present invention, separates the cylindrical, drilling portion from the threaded portion and two grooves or flutes which are preferably diametrically opposed to one another, extend from the annular groove to the pointed end of the cylindrical portion. The flutes serves as a passageway for the drilled chips which are directed out and away from the cutting edge and away from the hole being drilled as well as providing a passageway for the fluid. It should be understood that any reasonable number of flutes and ears may be used, although two of each will be illustrated and described hereinafter.

When the ears of the combination drill and plug break through the lead inner wall of the sleeve, the forward urging of the combination drill and plug pushes the plug of lead, now in the form of a disk that is trapped between the two ears and impaled by the sharp point, forward and away from the inside wall of the sleeve. This leaves an opening through which the fluid is free to flow into the flutes and then downward into the annular groove. From the annular groove, the fluid flows over the threaded portion of the combination drill and plug and over the driving socket and into a container which collects the fluid. If desired, the fluid may be directed by means of an opening in the container and a flexible tube into another, larger container, permitting the collection and testing of a fluid sample of any required quantity. After a suitable sample has been collected, the drill and plug combination is caused to be simultaneously urged forward and rotated so that the tapered threaded portion engages the sides of the hole and forms a mating thread in the lead sleeve. This effectively seals the opening. The plug of disk remains on the front end of the combination drill and plug. The fluid within the joint, therefore, is not contaminated by lead particles as a result of the drilling.

The apparatus comprising the present invention further includes a housing which positions, supports and guides the combination drill and plug. The housing also positions and supports the driving unit and provides a means for transmitting the power from the driving unit to the drilling and plugging portion through a clutch and a remote control unit. Attached to the housing are the electrical components required to connect a remote control box and the sensing devices that indicate completion of the several portions of the cycle comprising the method of the present invention. Also attached to the housing is clamping means for attaching the apparatus of this invention to the joint or splice of the electrical cable.

The method of the present invention is initiated by pushing downwardly on the combination drill and plug driving socket until an arming pin rides over the top of a stop thrust bearing contained within the housing thereby holding the stop thrust bearing, an intermediate shaft, an output shaft and the drive socket in a fully retracted position. A combination drill and plug is then placed in the driving socket and the apparatus is attached to the joint sleeve by means of a chain and two take-up screws. The apparatus may be adjusted sideways if necessary to position the combination drill and plug so that it is centered on the joint or splice before tightening the take-up screws. After positioning and tightening, a remote control box cable is connected to the machine and the arming pin is pulled out so that it moves off the top of the stop thrust bearing thereby permitting the shaft, the drive socket and the combination drill and plug to advance until the point of the combination drill and plug contacts and slightly penetrates into the lead sleeve of the joint or splice. A power switch on the remote control box is then moved to the "on" position. By pressing a start button on the remote control box, a motor is started and continues to drive the shaft, through a clutch assembly, which in turn causes the combination drill and plug to commence the drilling portion of the cycle.

An important aspect of the present invention is the combination of a drive shaft which is capable of moving axially, thus carrying with it and imparting both a rotating and an axial displacement to the combination drill and plug as well as a clutch which will slip or otherwise become disengaged when the combination drill and plug has been inserted into the sleeve to the proper depth. The drive shaft comprises a main drive shaft that is integral with an upper clutch plate, an intermediate shaft and an output shaft which carries the stop thrust bearing. The intermediate and the output shafts each are free to slide axially in relation to the other two shaft sections. The intermediate shaft and the output shaft sections are each urged forward by a coil spring through limited axial movement that is determined by a dowel pin which is fixed to the intermediate shaft which is free to move forward and backward within the confines of slots formed axially in each of the main drive shafts and the output shaft. The main drive shaft does not move axially. When the dowel pin is at an uppermost, extreme position in the main shaft, and in the uppermost position of the output shaft slot, the annular groove of the combination drill and plug will be located just below the surface of the joint sleeve thereby permitting fluid to drain out of the joint. The spring that imparts the drilling pressure is placed between the main drive shaft and the intermediate drive shaft in order to urge the intermediate drive shaft to a normally upward position with the dowel pin reaching the limit of its travel at the top of the slot in the main drive shaft. The second or plug setting spring is lighter and imparts a smaller force than the drilling pressure spring and is positioned between the intermediate shaft and the output shaft in order to urge the outer shaft to its uppermost position with the dowel pin resting at the bottom of the slot in the output shaft. Because of the greater force exerted by the drilling pressure spring, any resisting force applied to the combination drill and plug will hold the output shaft from moving upward in relation to the intermediate shaft while the intermediate shaft can still move upward to the limits of its travel carrying the output shaft with it in a retracted position. Since a greater axial force is required for drilling than for moving the combination drill and plug upwardly into the drilled hole, the intermediate shaft and the drilling pressure spring are used for that portion of the cycle. Means are also provided for varying the drilling pressure.

As the combination drill and plug passes into the wall of the joint sleeve, the intermediate shaft, which carries the output shaft in the retracted position, advances until the dowel pin reaches the limit of its travel. At the same time, the stop thrust bearing, which rests against a shoulder on the output shaft, is moved upwardly with the two shafts and comes to rest against the underside of a set plug pin. At this point, the combination drill and plug will have broken through the inner wall of the joint sleeve and no longer will there be a resistive force working against it. Consequently, the output shaft will not be maintained in its retracted position. The set plug pin now acts as the restraining force. Also, in this position, the fluid in the joint is free to flow down the flutes and into the annular groove of the combination drill and plug so that it may be collected in the sample container. Alternatively, the fluid may be passed through a discharge tube and collected in another, larger container. Approximately at the same time that the stop thrust bearing contacts the set plug pin, the sensing pin which indicates that the drilling has been completed, is pushed radially outward by an angled tip of the pin riding over a rounded edge of the stop thrust bearing. The movement of the pin actuates a switch causing the motor to stop and, at the same time, operates an indicator light on the remote control box to advise the operator that the drilling portion of the cycle has been completed and that the fluid should be flowing from the joint.

When asample of sufficient volume has been collected, a "set plug" button on the remote control box is pressed in order to resume operation. The pressing of the "set plug" button causes the motor to start and, at the same time, energizes a solenoid which pulls the set plug pin outwardly and away from the stop thrust bearing. This releases the output shaft so that it is now free to move axially upward while it is rotating, thus causing the threaded portion of the combination drill and plug to enter the drilled hole and to form mating threads in the wall in order to sealingly retain the combination drill and plug. At approximately the same time that the dowel pin reaches the limit of its travel in the output shaft slot, the sensing pin which indicates that the combination drill and plug has been inserted to its proper depth in the sleeve, is moved outwardly in the same manner as the first sensing pin. This actuates another switch which operates another indicator light on the remote control box, thereby advising the operator that the entire operation has been completed. The same pin and switch may also be used to stop the motor or the motor may be stopped manually.

As the combination drill and plug is inserted into the hole, the tapered thread forms the wall material into a mating tapered thread. As the combination drill and plug advances and the thread diameter increases, the required driving torque also increases. Finally, at the desired depth of insertion, the torque required to continue driving equals or exceeds the torque setting of the clutch so that the clutch then slips. This permits the upper clutch plate and the integral main drive shaft to stop rotating even though the motor may still be operating and driving the lower clutch plate.

The main drive shaft is positioned within the housing by a slidable sleeve bearing at its lower end and by a main bearing at its upper end. The main drive shaft rests upon the main bearing housing which covers and rests upon the main bearing. The main bearing in turn rests upon a thrust pad, which rests upon a shoulder of the housing. A retaining ring serves to transfer the downward axial load due to drilling pressures and the weight of the shaft and its associated components to the main bearing housing. A key locks the main bearing housing to the main drive shaft causing the shaft, the main bearing housing and the main bearing upper race to rotate as a unit. The lower race of the main bearing, resting on the thrust pad, does not rotate.

Clutch torque is developed by squeezing the clutch friction disk between the upper and lower clutch plates. The lower clutch plate is driven by the motor while the upper clutch plate is driven by the friction disk. Since the upper clutch plate is attached to or is otherwise formed integrally as a part of the main drive shaft, the entire shaft assembly is caused to rotate. By tightening a clutch adjusting nut, a clutch spring located between the nut and the lower thrust bearing is compressed thereby applying an axial force to the assembly that includes the main drive shaft and the clutch adjusting nut on one side and the lower thrust bearing, slidable sleeve bearing, the upper thrust bearing and the lower clutch plate on the other side. Since the main drive shaft is in an axially fixed position, it cannot be forced downwardly while the components on the other side of the spring are all slidably mounted on the shaft and within the housing. Therefore, the bearing on the lower clutch plate will be forced upwardly in relation to the main drive shaft and its integrally attached upper clutch plate and will thus squeeze the friction disk between the two clutch plates. Tightening the clutch adjusting nut increases the output torque.

It is, therefore, an object of the present invention to provide improved apparatus, as described above, for extracting a fluid sample from an electrical cable or the like.

It is another object of the present invention to provide an improved method, as described above, for extracting a fluid sample from an electrical cable or the like.

It is a further object of the present invention to provide a combination drill and plug that may be used with the foregoing method and apparatus comprising the present invention.

It is yet another object of the present invention to provide improved apparatus and a method for operating same for removing a test sample of fluid from an electrical cable or the like without contaminating the fluid in the cable with metal chips that result from the drilling operation.

It is a still further object of the present invention to provide an improved method and apparatus for removing a test fluid sample from an electrical cable or the like, which method and apparatus may be operated remotely at a minimum cost and with minimum personnel.

The above description, as well as further objects, features and advantages of the present invention, will be more fully appreciated by reference to the following detailed description of a presently preferred, but nonetheless illustrative embodiment, in accordance with the present invention when taken in conjunction with the accompanying drawings.

BRIEF DESCRIPTION OF THE DRAWINGS

In the drawings, wherein the same reference numeral denotes the same element throughout the several views.

DETAILED DESCRIPTION OF THE INVENTION

Figure 1:
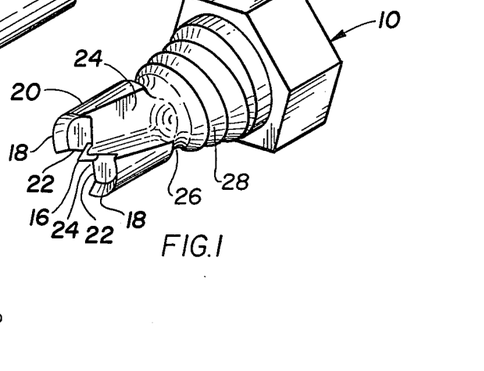
FIG. 1 is a perspective view of the novel combination drill and plug comprising the present invention.

Referring now to the drawings and particularly to FIG. 1, there is shown a combination drill and plug 10 comprising one aspect to the present invention. The combination drill and plug 10 is used to drill through the cable joint sleeve 12 (FIG. 2) utilizing apparatus generally designated by the reference character 14 in FIG. 2. The combination drill and plug 10 seen in detail of FIG. 1 comprises a pilot point 16, slicing ears 18 and a drill portion 20. The leading end of the drill portion 20 has cutting edges 22 and drill-like flutes 24 that extend in a generally axial direction. At the opposite end of the drill portion 20, an annular groove 26 is used to separate the drill portion 20 from a tapered thread 28. A drive head 30, which may be hexagonal shape, completes the combination drill and plug unit 10.

Figure 2:
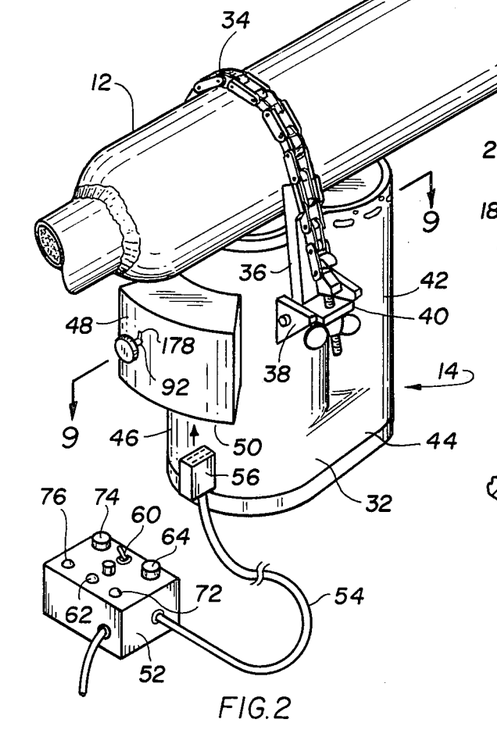
FIG. 2 is a perspective view of the apparatus comprising the present invention secured to a cable joint sleeve.

As shown in FIG. 2, the apparatus 14 comprising the present invention is strapped to the cable joint sleeve 12. A main housing 32 is supported by a chain strap 34 and a pair of alignment arms 36, only one of which is shown in FIG. 2. Suitable brackets 38, combined with clamping means 40, permit accurate location and firm support of the apparatus 14. One portion of the housing 32 defines a motor housing 42, the lowermost section of which defines a gear train housing 44. Another portion 46 of the housing 32 contains the drive mechanism for the combination drill and plug 10. A sub-housing 48, which may be made of sheet metal, contains electrical apparatus. On the lower surface of the sub-housing 48, there is provided a polarized connecting means 50 which facilitates the connection of a control box 52 by means of a cable 54 and a receptacle 56.

Figures 3, 4, 6, 7:
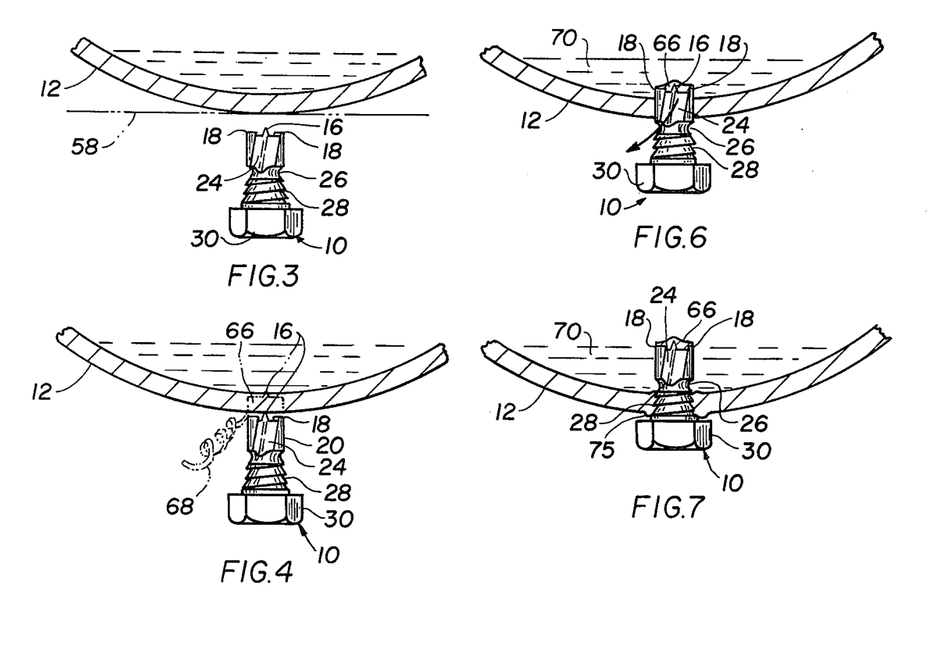
FIG. 3 is a fragmentary, schematic view, partially in section, illustrating the first step in the method comprising the present invention.
FIG. 4 is a view similar to FIG. 3 illustrating still another step in the method comprising the present invention.
FIG. 6 is an additional schematic view illustrating still another step in the method comprising the present invention.
FIG. 7 is a fragmentary sectional elevational view illustrating the novel combination drill and plug comprising the present invention at the completion of the cycle.

FIGS. 3-7 will be used to illustrate the sequence of steps in the method comprising the present invention. In FIG. 3, the combination drill and plug 10 is in the fully retracted position. The tangent line 58 shown in phantom in FIG. 3 represents the top surface of the housing 32. This position of the combination drill and plug 10 provides for easy mounting of the apparatus 14 on the cable joint sleeve 12. In FIG. 4, the combination drill and plug 10 is shown moved into a "ready position". The pilot point 16 is in contact with the cable joint sleeve 12 and may penetrate the lead sleeve to some slight degree. At this stage of the cycle, the operator will then retreat to and position himself in a remote location in order to turn on a power switch 60 in the remote control unit 52. A pilot light 62 indicates that power is on. A "drill" button 64 is then pressed and the combination drill and plug 10 rotates. Because of spring pressure which will be described hereinafter, the combination drill and plug 10 advances gradually into the sleeve 12. The slicing ears 18 contact the sleeve and are then followed by the cutting edges 22 which shave chips 68 (FIG. 4) from the outermost face of the disk or plug 66 which is generated by the slicing ears 18. Rotation of the combination drill and plug 10 continues approximately to the position shown in phantom outline in FIG. 6.

Figure 5:
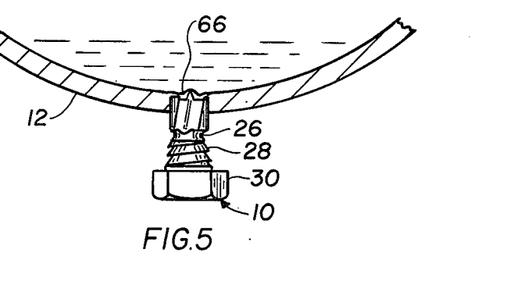
FIG. 5 is a schematic view similar to FIGS. 3 and 4 illustrating still another step in the method comprising the present invention.

As shown in FIG. 5, cutting by the drill portion 20 stops and a shearing action takes place due to spring forces which will be described hereinafter. The shearing action then moves to the drill plug 10 to its position in FIG. 6 at which time sensing means stops the rotation of the combination drill and plug and a pilot light goes "on". FIG. 6 illustrates the combination drill and plug 10 in an advanced, predetermined position after shearing through the cable joint sleeve 12. The remainder of disk 66 is caught and held wedged between the slicing ears 18 and impaled on the pilot point 16 so as not to fall into and contaminate the insulating oil 70 within the cable joint sleeve 12.

At this point the drive motor has been turned off and a pilot light 72 indicates that the drill cycle has been completed. Oil 70, under slight nitrogen pressure, is forced through the flutes 24, into and around the annular groove 26 of the combination drill and plug 10, and into a suitable sample cup container 102 for subsequent laboratory analysis of moisture content. When it has been determined that an adequate sample of oil 70 has been drawn off, a "set-plug" button 74 on the remote control unit 52 is pushed so that the combination drill and plug 10 is again rotated and advanced until it reaches the position shown in FIG. 7. As the tapered thread 28 moves through the wall of the cable joint sleeve 12, there is a local upsetting bead 75 and working of the lead metal adjacent the thread to ensure a fluid-tight seal between the bead 75 and head 30. Sensing means stop the drive motor when the combination drill and plug end comes to its final position and the pilot light 74 shows that the "set-plug" cycle has been completed.

Figures 8, 10, 11:
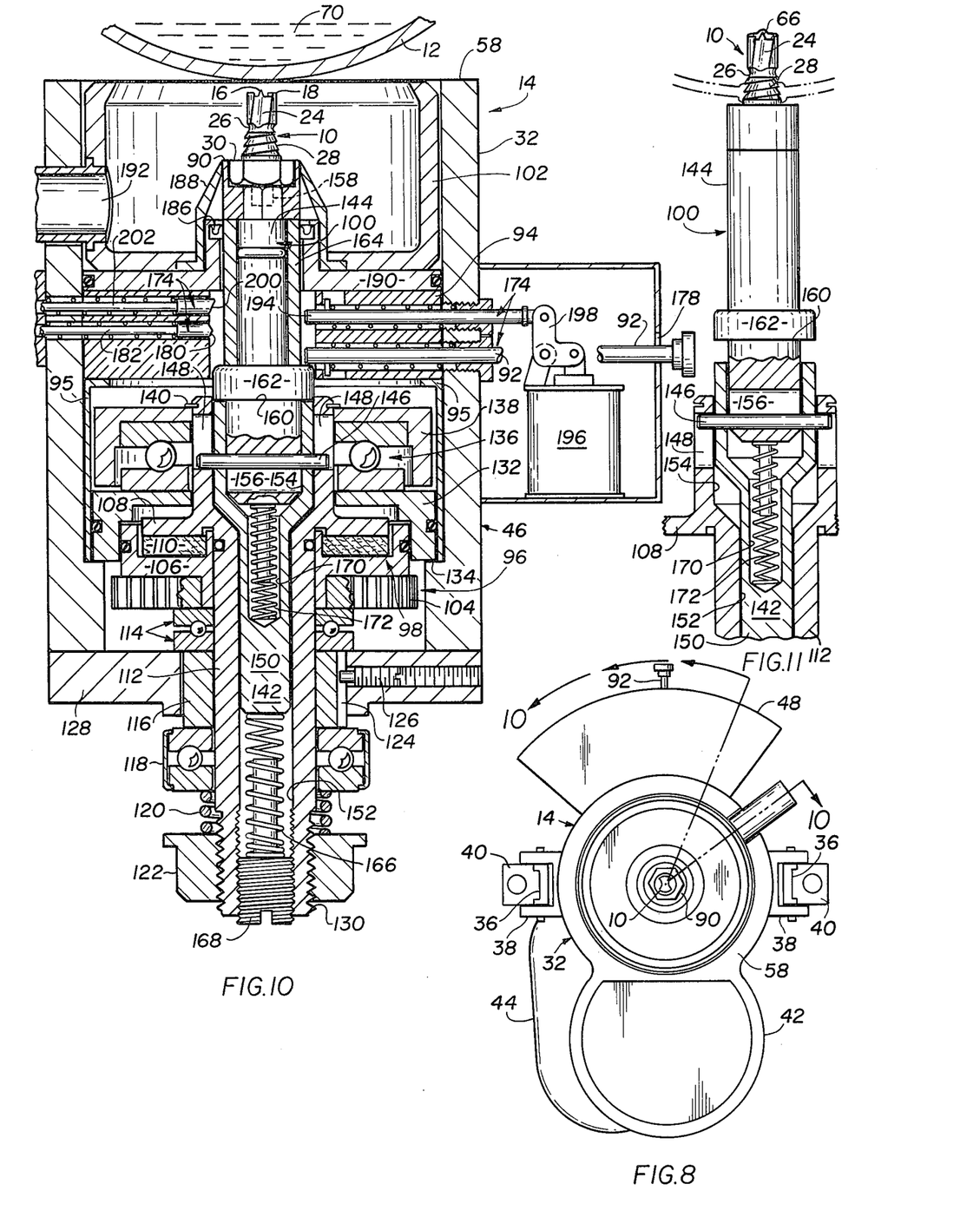
FIG. 8 is a plan view of the apparatus shown in FIG. 2 with the cable joint sleeve removed for clarity.
FIG. 10 is a longitudinal, sectional elevational view taken along line 10—10 of FIG. 8.
FIG. 11 is a fragmentary longitudinal elevational view, partially in section, illustrating a second position of the structure shown in FIG. 10.

FIG. 8 illustrates the apparatus 14 ready to be mounted on the cable joint sleeve 12 with the chain strap 34 removed for clarity. The combination drill and plug 10 has been inserted into a drive socket 90 as in FIG. 10. The combination drill and plug 10 as well as the drive socket 90 have been manually forced into a fully retracted position and held in place by an arming pin 92, which position is also shown in FIG. 10.

Figure 9:
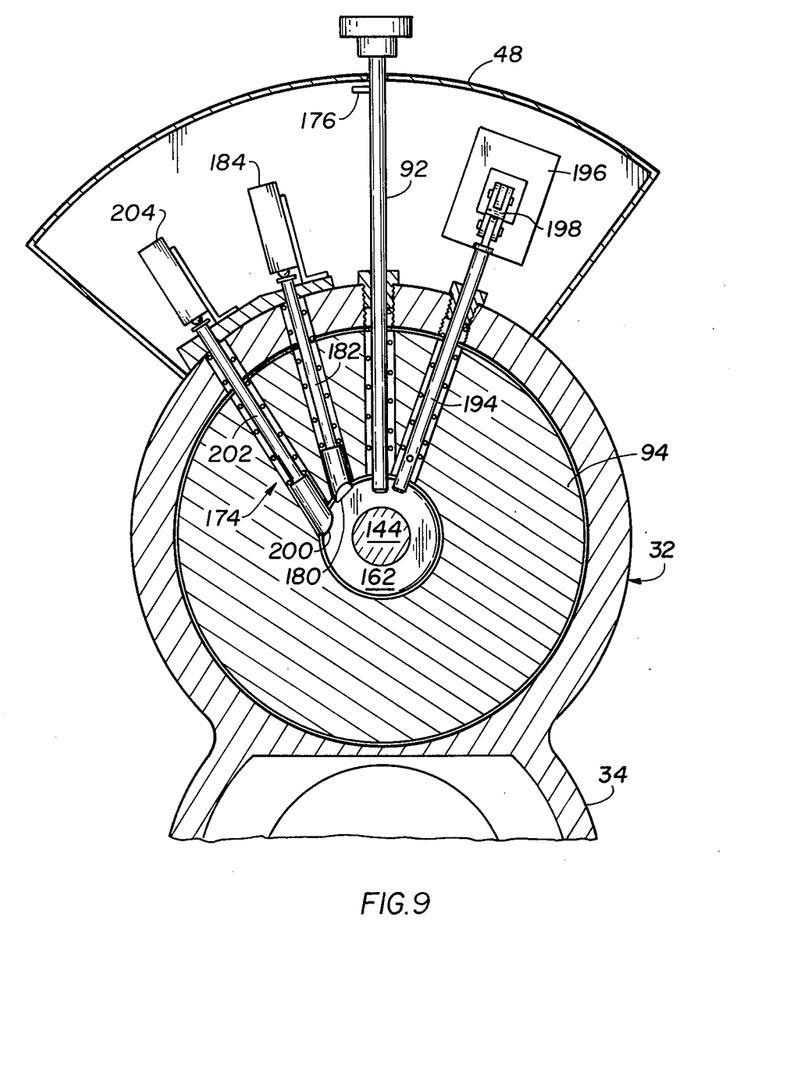
FIG. 9 is a sectional plan view taken along line 9—9 of FIG. 2.

Section lines 9—9 in FIG. 2 pass through a control and sensing pin block that guide four control pins. FIG. 9 is used to illustrate the relative radial deployment of the control pins with respect to each other. However, it is to be understood that the control pins are at different levels such as shown in FIG. 10. It should be further noted that FIG. 10 is intentionally distorted so as to reveal the vertical displacement of the four control pins.

Referring now to FIG. 10, it will be seen that the drive housing 32 contains a power drive section 96, a clutch 98, a three section telescoping drive shaft 100, the control pin block 94 and a sample collecting container 102. Various set screws, seals, sleeves, springs, spacers and bearings make up the remainder of the unit and will be described in more detail hereinafter. It should be noted at this time that all electrical components are standard and are utilized in their usual manner.

It is a feature of the present invention that the apparatus 14 eliminates any back pressure on the combination drill and plug 10 in such a way that it will have no effect on the maximum torque output on the clutch section 98. In other words, the maximum torque of the clutch section 98 will not be influenced in any way as the combination drill and plug 10 proceeds through the various steps of the method comprising the present invention.

The power drive section 96 is comprised of a motor (not shown), a gear train (not shown), and a clutch drive gear 104 which is permanently attached to the lower clutch plate 106 that represents one element of the clutch section 98. Sandwiched between an upper clutch plate 108 and the lower clutch plate 106 is a clutch disk 110. Since the main drive shaft 112 is integral with the upper clutch plate 108, it serves as a tension member to provide the necessary clutch pressure. This pressure is developed via an upper thrust bearing 114, a sleeve bearing 116, a lower thrust bearing 118, a clutch spring 120, and a clutch adjusting nut 122. The clutch adjusting nut 122 may be tightened to compress the spring 120 which results in forcing the upper and lower clutch plates 108 and 106, respectively, against the clutch disk 110. Thus, there is developed an adjustable maximum torque to be delivered to the combination drill and plug 10. The lower race of the upper thrust bearing 114 and the upper race of the lower thrust bearing 118 are held in frictional contact with the sleeve bearing 116 which is provided with a key slot 124 therein in order to receive a retaining screw 126 that prevents rotational movement of these elements. The clutch adjusting nut 122 may be adjusted on threads 130 to suit various conditions.

A thrust pad 132 surrounds the clutch section 98 and rests on a shoulder 134 within the housing 32. A main bearing 136 rests upon the thrust pad 132 and cooperates with the upper end lower thrust bearings 114 and 118 supporting the main drive shaft 112 for stable rotation. A main bearing housing 138 surrounds the main bearing 136 and is held by a clamp ring 140.

In addition to the aforementioned main drive shaft 112, the three section telescoping shaft 100 is further comprised of an intermediate shaft 142 and an output shaft 144. A dowel pin 146 serves to coordinate the relative movement of the three shaft elements 112, 142 and 144 and transmits torque from the main drive shaft 112 to the combination drill and plug 10. The pin 146 is fixed in longitudinal relationship to the intermediate shaft 142. The outer ends of the pin 146 are confined within elongated, axially oriented slots 148 which are located in the upper wall of the main drive shaft 112. The vertical length of these elongated slots 148 approximate the vertical movement of the combination drill and plug 10 during the drilling and sampling phase of the method comprising the present invention.

The intermediate shaft 142 has a lower extension 150 which fits into a bore 152 formed in the lower end of the main drive shaft 112. The upper, bell-shaped end of the intermediate shaft 142 has a recess 154 that is sized to receive the lower end of the output shaft 144. The pin 146 passes through an elongated, vertically oriented slot 156 in the lower end of the output shaft 144. The vertical length of the slot 156 approximates the distance that the combination drill and plug 10 advances between the sampling stage of the cycle of operation and the final setting of the combination drill and plug 10. It should be noted at this time that FIG. 10 illustrates the three element shaft 100 in a fully retracted position while FIG. 11 illustrates three element shaft 100 in a fully extended position.

The keyed drive socket 90 is suitably formed to fit onto the upper end of the output shaft 144 as well as to receive the head 30 of the combination drill and plug 10. A retaining magnet 158 may be imbedded in the shaft 144 to enhance the holding power of the drive socket 90.

The output shaft 144 is provided with a shoulder 160 on which a stop thrust bearing 162 is mounted. An output shaft bearing 164 holds the bearing 162 in place vertically. A drilling pressure spring 166 is located in the lower end of the main drive shaft 112 within the bore 152 and bears against the intermediate shaft 142 and a drilling pressure adjusting screw 168. The adjustment of the screw 168 within the main shaft 112 determines the force with which the combination drill and plug 10 is urged against the cable joint sleeve 12 during the drilling and breakthrough phases of the method comprising the present invention.

The intermediate shaft 142 isprovided with a cavity 170 in which a plug setting spring 172 is confined. The plug setting spring 172 provides the force necessary to urge the combination drill and plug 10 into the cable joint sleeve 12 in order to engage the tapered thread 28.

As shown in FIG. 9, an array of four control pins, generally designated by the reference character 174, are used in cooperation with the combination drill and plug 10. It should be noted at this time that all four control pins 174 are spring biased towards the center and that the pin block 94 is supported on a flanged ring 95.

As mentioned hereinabove, a first step in the operation of the apparatus 14 is to retract the drive socket 90 on the shaft 100 to its lowermost position as shown in FIG. 10. The operator can manually depress the drive socket 90 and allow the spring biased arming pin 92 to lock on the upper shoulder or surface of the stop thrust bearing 162. A combination drill and plug 10 is then inserted into the drive socket 90 and releasably held by the magnet 158. The apparatus 14 may then be strapped in position on the cable joint sleeve 12 as shown in FIGS. 2 and 3 and may then be connected to the control box 52. The arming pin 92 is then pulled outwardly to release the stop thrust bearing 162. The arming pin 92 is fitted with a lockout pin 176 to keep it in the "out" position. After the lockout pin 176 passes through a slot 178 (FIGS. 2 and 10), a quarter turn of the arming pin 92 will lock out the pin 176.

The drilling pressure spring 166 forces the shafts 142 and 144 upwardly until the combination drill and plug 10 contacts the cable joint sleeve 12 as shown in FIG. 4. The operator at this point then presses the drill button 64 which results in the turning and drilling of the combination drill and plug 10 via the shaft assembly 100, the clutch section 98 and the power drive section 96. The combination drill and plug 10 is allowed to pierce the cable joint sleeve 12 and arrive at the position shown in FIG. 6. In so doing, the stop thrust bearing 162 bears against a cam surface 180 of a "drilling complete" sensing pin 182 which in turn activates a switch 184 to stop the motor and to turn on the pilot light 72. The upper face of the stop thrust bearing 162 now comes to rest against a "set plug" pin 194.

The oil sample 70 is now allowed to collect in the container 102. A seal gland 186 is mounted in the hub section 188 of the container 102 to keep the oil 70 from getting into the shaft section 100. An additional seal plate 190 further provides for this function. An optional outlet 192 may be provided to direct the oil sample to another container (not shown).

When an adequate oil sample has been collected, the operator presses the "plug set" button 74 which starts the motor and turns the shaft 100. Simultaneously, a solenoid relay 196 is activated to pull the "set plug" pin 194 away from the stop thrust bearing 162 by means of a bell crank linkage 198 thereby allowing the output shaft 144 to be urged upwardly by the plug setting spring 172.

The final position of the combination drill and plug 10 is determined by the stop thrust bearing 162 pressing against a cam face 200 of a "set plug" sensing pin 202 which activates a switch 204. This action shuts the motor off and turns on the pilot light 76 indicating that the cycle has been completed.

Should the thread resistance exceed the torque setting of the clutch, the upper clutch plate 108 will slip while the lower clutch plate 106 continues to be driven. In this case, the operator will shut down the motor manually.

Clutches other than that which has been illustrated and described may be used, such as displacement, electro-magnetic, magnetic particle, hydraulic, pneumatic, etc. Other sensing means also may be used to control the motor and the clutch as well as to indicate the position of the combination drill and plug. For instance, probes may be used to contact the surface of the joint sleeve and, by having its upward movement restricted, it could be made to operate a switch to cut off power to the motor and the clutch or it could close an electrical circuit merely by contacting the metallic sleeve. The arming pin and the "set plug" pin also may be operated by other means such as pneumatically, hydraulically, a push-pull flexible cable, etc. The driving socket could be urged upwardly by means other than springs, for instance, hydraulically or pneumatically and the three-piece drive shaft need not be used as long as other means for moving and controlling the position of the combination drill and plug is provided. It should also be noted that the combination drill and plug as well as the entire apparatus may be used on materials and shapes other than lead cylinders.

While there have been shown and described and pointed out the fundamental novel features of the invention as applied to the preferred embodiment thereof, it will be understood that various omissions and substitutions and changes in the form and details of the device illustrated and its operation may be made by those skilled in the art without departing from the spirit of the invention. It is the invention, therefore, to be limited only as indicated by the scope of the claims appended hereto.

What is claimed is:

1. A combination drill and plug comprising a drive means having a body with means thereon for removing a mass of material to make an opening, said removing means being a cutting means comprising at least one arcuate segment defining an ear having a cutting portion at the leading edge thereof in the direction of rotation to form a disk of the removed material, said ear engaging the disk of removed material to retain the same on said removing means, thread forming means on said drive means coextensive with said removing means for engaging the wall of the opening formed by the removal of material, plug means coextensive with said thread forming means including means to plug the opening, and means engageable with said drive means for rotating and axially advancing said removing means, said thread forming means and said plug means to remove the disk of material during the making of an opening, threading the opening and then plugging the opening to close the same while the disk of removed material is retained on said removing means and removable from engagement therewith after the opening is plugged closed.

2. A combination drill and plug as claimed in claim 1 wherein said cutting means further includes an axially oriented point at the end thereof, said point being arranged to penetrate and thereby further assist in the retention of the disk of removed material.

3. A combination drill and plug as claimed in claim 1 wherein there are two of said arcuate segments.

4. A combination drill and plug as claimed in claim 1 wherein said cylindrical portion further includes edge means at the ends thereof for cutting away and thereby reducing the thickness of the disk or removed material.

5. A combination drill and plug as claimed in claim 1 wherein there is further included an annular groove intermediate said cutting means and said thread forming means.

6. A combination drill and plug as claimed in claim 5 wherein there is further included at least one flute extending generally axially from the end of said cutting means into fluid communication with said annular groove.

7. A combination drill and plug as claimed in claim 6 wherein there are two of said flutes.

8. A combination drill and plug as claimed in claim 1 wherein said thread forming means comprises an axially threaded section intermediate said cutting means and said rotating means.

9. A combination drill and plug as claimed in claim 8 wherein said threaded section is tapered.

10. Apparatus for removing a fluid sample from the interior of a cable or the like, said apparatus comprising:

cutting and plugging means for first providing a hole through the wall of the cable to permit the removal of fluid from the cable and for subsequently plugging the hole after a desired quantity of fluid has been removed;

axially displaceable and rotatable shaft means for supporting and positioning said cutting and plugging means adjacent the exterior surface of the cable;

drive means for advancing and rotating said cutting and plugging means to cause the same to form the hole through the wall of the cable whereby the selected quantity of fluid may drain from the cable and for advancing and rotating said cutting and plugging means for plugging the hole after the desired quantity of fluid has been removed from the cable whereby additional fluid is prevented from leaking out of the cable, sensing means operable in response to the advancement of said shaft means, and means for stopping said drive means when said sensing means senses that said shaft means and said cutting and plugging means have advanced sufficiently to provide the hole and to completely plug the hole after the desired quantity of fluid has been removed from the cable.

11. Apparatus as claimed in claim 10 wherein said shaft means comprises a first, non-axially displaceable main section and an intermediate and an output section both of which are axially movable relative to the other, and there being further included means for biasing and intermediate and said output shaft sections relative to each other, and means for limiting the relative movement thereof.

12. Apparatus as claimed in claim 11 wherein said movement limiting means comprises an axially elongated slot in said main shaft section and in said output shaft section and a pin rigidly secured to said intermediate shaft section, said pin being in engagement with said slots in said main shaft section and in said intermediate shaft section, whereby when said pin is at one extreme position in said slots said cutting and plugging means is at a depth that permits fluid to be removed from the cable.

13. The apparatus asclaimed in claim 11 wherein said means for biasing said intermediate shaft has a greater force than said means for biasing said output shaft.

14. Apparatus as claimed in claim 11 and further including clutch means intermediate said shaft means and said drive means, said clutch means being arranged to disengage when said cutting and plugging means has plugged the hole.

15. Apparatus as claimed in claim 14 wherein said clutch means comprises a first clutch plate integral with said main shaft section, a second clutch plate rotated by said drive means and a friction plate intermediate said first and said second clutch plates for rotatingly driving said first clutch plate.

16. Apparatus as claimed in claim 14 and further including means for increasing and decreasing the output torque of said clutch means.

17. Apparatus as claimed in claim 10 wherein said cutting and plugging means comprises a first section having cutting edge means for removing a mass of material from the cable in the form of a disk and to enable the removal of fluid from the cable, and a second coaxial threaded section adapted to be rotated and advanced into the hole formed by said cutting edge means to thereby form a mating thread in the wall of the cable whereby the hole is sealed and further fluid leakage is prevented.

18. Apparatus as claimed in claim 17 wherein said first section includes at least one generally axially extending flute for assisting in the removal of fluid from the cable.

19. Apparatus as claimed in claim 17 wherein said first section includes means for retaining on said cutting and plugging means the disk of material removed from the cable.

20. Apparatus as claimed in claim 10 and further including means for receiving the fluid removed from the cable.

21. In an apparatus for attachment to and for sampling the oil content of an electrical cable and for resealing the cable and for removal therefrom without disabling the cable, operable means for forming a hole in the cable through which a desired sample of oil may flow from the cable by removing a portion of the cable and including means to retain thereon the removed cable portion to prevent the same from falling into the oil of the cable, means on said apparatus positioned adjacent the hole for receiving the oil sample as the same flows therethrough from the cable, means on said apparatus for operating said operable means to form the hole in the cable and for operating said operable means to close the hole to seal the cable thereat from the further flow of oil, and means on said apparatus to attach the same to an electrical cable and for removal therefrom including said oil sample receiving means especially after operating said operable means to close the cable hole.

22. A method for removing fluid from a cable and thereafter sealing the cable, said method comprising the steps of:

positioning an apparatus including fluid receiving means and a combination cutting and plugging tool adjacent the exterior surface of the cable;

advancing the tool through the cable wall to form a hole therein whereby fluid may be discharged from the cable into the fluid receiving means while removing a mass of material from the cable wall in the form of a disk and retaining the disk of removed material on the tool to prevent the same from falling into the cable;

thereafter advancing the tool through the cable wall thereby the tool seals the hole in the cable to take the place of the removed material and thereby prevent further leakage of the fluid from the hole, and removing the apparatus including the fluid receiving means from adjacent the exterior surface of the cable.

23. A method as claimed in claim 22 wherein said first advancing step comprises the steps of rotating the tool whereby material is cut from the cable to form the hole.

24. A method as claimed in claim 22 wherein said second advancing step comprises the step of rotating the tool whereby the tool forms thread into the wall of the cable to cause the tool to fluid tightly engage the cable and seal the hole.

25. A method as claimed in claim 22 and further including the steps of sensing the removal of a mass of material from the wall of the cable and halting said first advancing step.

26. A method as claimed in claim 22 and further including the steps of sensing the completion of the sealing of the tool to the cable and halting said second advancing step.

* * * * *

UNITED STATES PATENT OFFICE
CERTIFICATE OF CORRECTION

PATENT NO. : 4,046,013
DATED : September 6, 1977
INVENTOR(S) : Cyril Robert Green It is certified that error appears in the above-identified patent and that said Letters Patent are hereby corrected as shown below:

IN THE CLAIMS:

Claim 11, line 6, change first "and" to --said--

Claim 22, line 15, change "thereby" to --whereby--

Claim 23, line 2, change "comprises the steps" to --comprises the step--

Claim 24, line 3, change "thread" to --threads--

Signed and Sealed this

Sixth Day of December 1977

[SEAL]

Attest:

RUTH C. MASON
Attesting Officer

LUTRELLE F. PARKER
Acting Commissioner of Patents and Trademarks